United States Patent [19]

Bales

[11] Patent Number: 5,259,376
[45] Date of Patent: * Nov. 9, 1993

[54] TRACHEOSTOMY TUBE ASSEMBLY

[76] Inventor: Joseph H. Bales, 23991 Ironhead, Laguna Niguel, Calif. 92677

[*] Notice: The portion of the term of this patent subsequent to Oct. 8, 2008 has been disclaimed.

[21] Appl. No.: 711,185

[22] Filed: Jun. 5, 1991

Related U.S. Application Data

[63] Continuation of Ser. No. 588,764, Sep. 26, 1990, Pat. No. 5,054,482.

[51] Int. Cl.⁵ .......................................... A61M 16/00
[52] U.S. Cl. .......................... 128/207.17; 128/207.14
[58] Field of Search .................. 128/207.14, 207.17, 128/207.15, 207.16, 204.18, 207.29, 912, 200, 24; 623/9

[56] References Cited

U.S. PATENT DOCUMENTS

| | | | |
|---|---|---|---|
| 1,835,757 | 12/1931 | Burchett | 128/207.17 |
| 3,066,674 | 12/1962 | Capra | 623/9 X |
| 3,659,612 | 5/1972 | Shiley | 128/207.14 |
| 3,693,624 | 9/1972 | Shiley | 128/207.14 |
| 4,033,353 | 7/1977 | La Rosa | 128/207.15 |
| 4,064,882 | 12/1977 | Johnson | 128/207.15 |
| 4,146,034 | 3/1979 | Gupta | 128/207.14 |
| 4,152,017 | 5/1979 | Abramson | 128/207.14 X |
| 4,166,467 | 9/1979 | Abramson | 128/207.14 |
| 4,235,229 | 11/1980 | Ranford | 128/207.17 |
| 4,351,328 | 9/1982 | Bodai | 128/202.16 |
| 4,351,331 | 9/1982 | Gereg | 128/207.17 |
| 4,852,565 | 8/1989 | Eisele | 128/207.14 |
| 4,987,895 | 1/1991 | Heimlich | 128/207.14 |

FOREIGN PATENT DOCUMENTS

| | | | |
|---|---|---|---|
| 2848645 | 5/1979 | Fed. Rep. of Germany | 128/207.14 |
| 1207144 | 8/1959 | France | 128/207.14 |
| 2007789 | 9/1978 | United Kingdom | 128/207.14 |

OTHER PUBLICATIONS

Schreiner, Mark S., Kettrick, Robert G., Balderston, Philip, Downes, John J., Swivel-Connector System for Pediatric Tracheostomy; An Improvement, *Respir Care*, 1986, 31, 109–112.

Portex Catalog; "Blue Line Tracheostomy Tubes" Aug., 1986.

*Primary Examiner*—Edgar S. Burr
*Assistant Examiner*—Eric P. Raciti

[57] ABSTRACT

An improved tracheostomy tube is disclosed having an inferiorally angled or downwardly bent rotatable, pivotal external connector portion which will accomplish immediate downward bending of a ventilator tube at a point immediately adjacent the anterior aspect of a patient's neck. The tracheostomy tube is adapted to eliminate the forward extension of any appreciable amount of hardware from the patient's neck and will serve to avoid interference with the patient's chin as well as the resultant discomfort and potential disruption of the ventilator tubing.

33 Claims, 2 Drawing Sheets

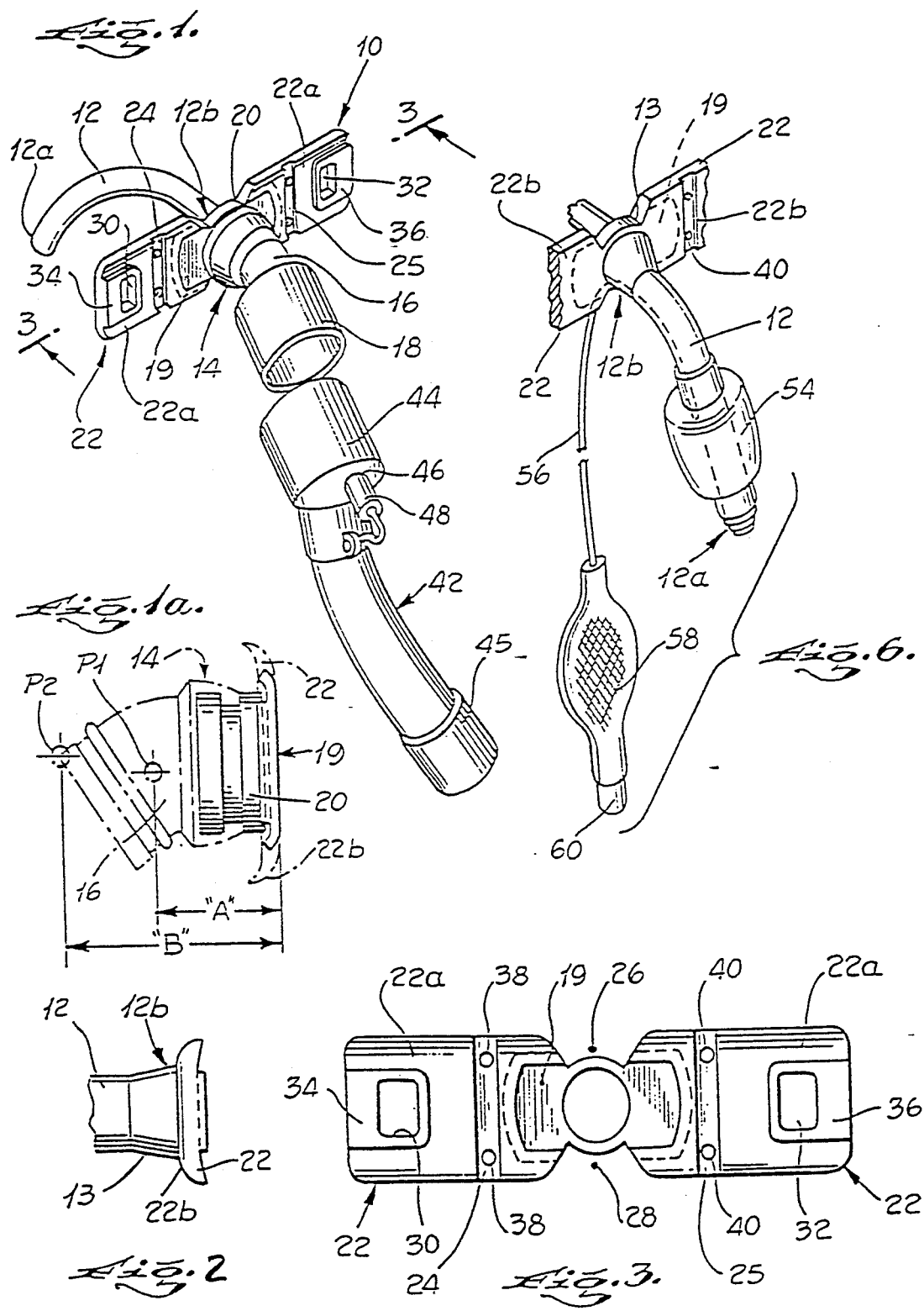

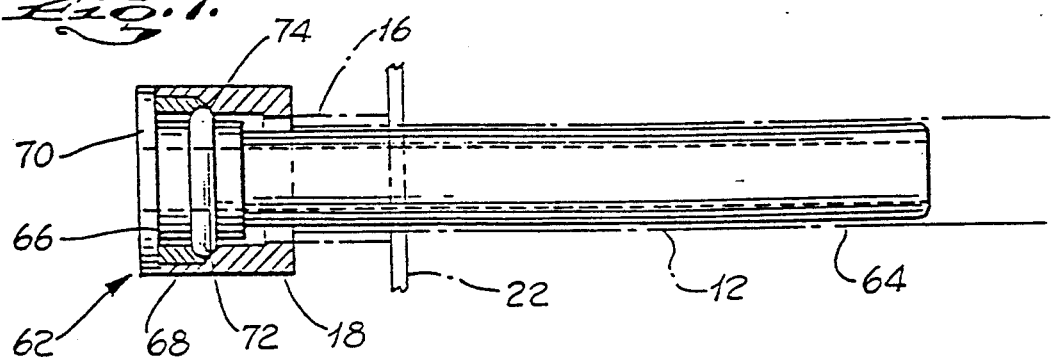
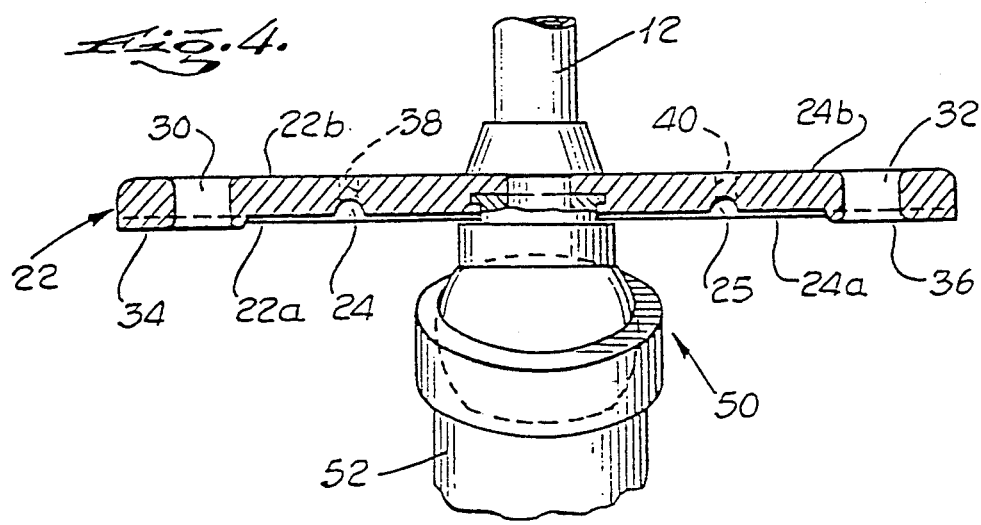
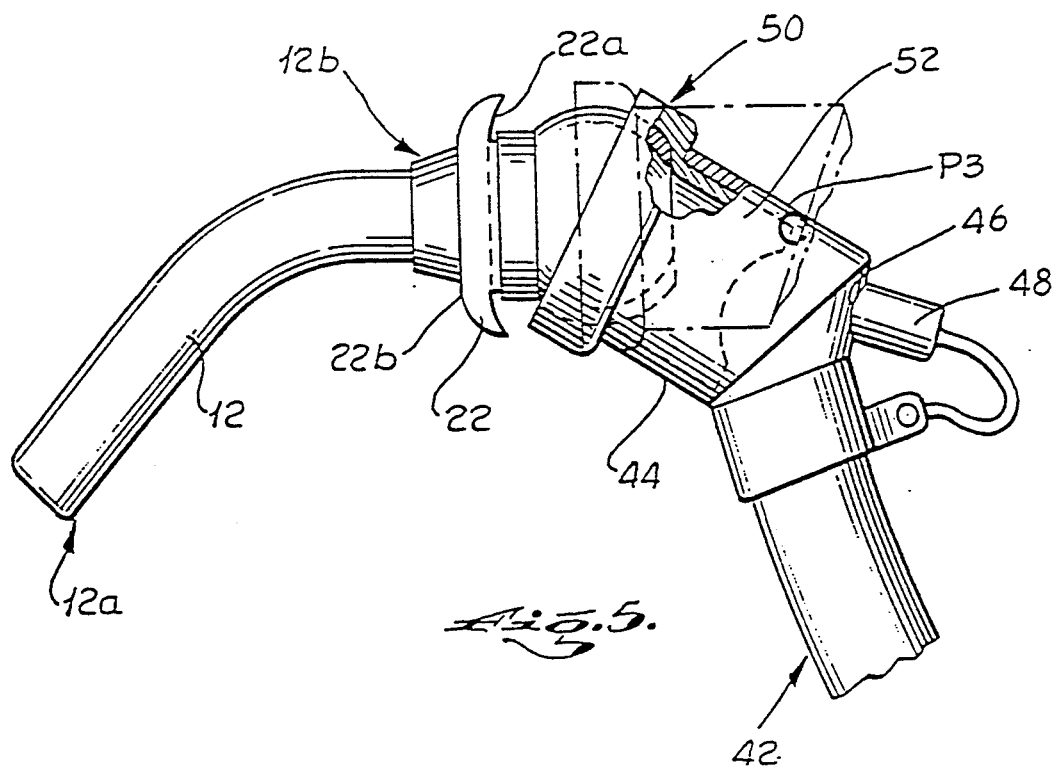

TRACHEOSTOMY TUBE ASSEMBLY

This application is a continuation of application Ser. No. 07/588,764, filed Sep. 26, 1990, now U.S. Pat. No. 5,054,482.

FIELD OF THE INVENTION

The present invention pertains generally to medical devices and more particularly to a tracheostomy tube assembly which is specifically configured and adapted to maximize patient comfort and to avoid contact of the tracheostomy tube assembly with the patient's chin.

BACKGROUND OF THE INVENTION

Numerous tracheostomy tubes are well known in the prior art. Such tracheostomy tubes typically comprise a cannula portion insertable through a tracheostomy into the trachea and an external connector portion which extends upwardly from the anterior aspect of the neck to permit connection of ventilator support tubing to the tracheostomy tube. Various angled connectors, elbows, etc. may be mounted on the external connector portion of the tracheostomy tube to facilitate operative connection and functional movement of an attendant ventilator tube thereto. In general, however, such tubing adapters, elbows, etc. result in a substantial mass of hardware being disposed immediately forward of the anterior aspect of the patient's neck. In many patients, especially neonates and infants, this mass of hardware extending directly outward from the anterior aspect of the neck causes interference with the patient's chin, thereby resulting in discomfort to the patient and potential interference and/or disruption of the ventilator connection.

In view of the above-stated shortcomings of the prior art tracheostomy tubes, there exists a need in the art for an improved tracheostomy tube assembly having an inferiorally angled or downwardly bent external connector portion which is at least partially rotatable or pivotal and which will accomplish immediate downward bending of the tube at a point immediately adjacent the anterior aspect of the neck. Such device will eliminate the forward extension of any appreciable amount of hardware and will serve to avoid interference with the patient's chin, as well as the resultant discomfort and potential disruption of the ventilator tubing.

SUMMARY OF THE INVENTION

In its basic embodiment, the present invention is a tracheostomy tube assembly comprising an arcuate cannula having a first end and a second end. The cannula is sized and configured to be insertable through a tracheostomy to an "operative" position, whereat the first end of the cannula resides within the trachea and the second end of the cannula is generally flush with the anterior aspect of the neck. A tubular elbow is provided which also defines a first end and a second end, the first end being connected to the second end of the cannula. Advantageously, the tubular elbow defines an inferiorally directed bend immediately adjacent the neck when the cannula is in the operative position. In this respect, the tubular elbow is adapted to permit operative connection of a ventilator tube to the cannula such that the ventilator tube will extend inferiorally away from the chin. The operative connection is facilitated by a ventilator tube connector which is mounted on the second end of the tubular elbow. In the preferred embodiment, the first end of the tubular elbow is pivotally connected to the second end of the cannula so as to avoid problems associated with movement of the ventilator tube which would tend to twist the ventilator tube and dislodge the tracheostomy tube. According to a second embodiment of the present invention, the tubular elbow is replaced by a ball and socket connector which is likewise operable to direct the ventilator tube inferiorally away from the chin.

In accordance with a further aspect of the invention, the tracheostomy tube of the present invention may comprise one or more neck flanges which extend laterally from the second end of the cannula such that the neck flange(s) may rest against the anterior surface of the neck when the cannula is in the operative position. The neck-contacting surface(s) of the flange(s) may be radiused or feathered so as to eliminate sharp edges which could cut into the underlying skin of the neck. The flange(s) may be further adapted to permit accessibility to the tracheostomy for purposes of cleaning, disinfecting, etc., and may include various apertures to be used in securing the flange(s) to the neck.

Further in accordance with the invention, there is provided an extension tube which is attachable to the ventilator tube connector of the tracheostomy tube. The extension tube may be curved or angled in an inferior direction such that it will extend downwardly from the ventilator tube connector of the tracheostomy tube to a point just above the anterior thorax of the patient. The extension tube may further include a suction catheter introduction port formed therein to permit passage of a suction catheter therethrough into the cannula.

Still further in accordance with the invention, there is provided an inner cannula assembly which may be inserted into the ventilator tube connector and cannula portions of the tracheostomy tube assembly. Since phlegm and mucus often form within and have a tendency to clog the tracheal tubing, one of the primary purposes of the inner cannula is to allow the cleaning of the tracheal tubing without removal of the whole tracheostomy tube assembly from the patient.

Further aspects and advantages of the invention will become apparent to those skilled in the art upon reading and understanding the following detailed description and the accompanying drawings.

BRIEF DESCRIPTION OF THE DRAWINGS

FIG. 1 is a perspective view of the tracheostomy tube assembly of the present invention;

FIG. 1a is a side elevational view of a portion of the tracheostomy tube assembly of the present invention, illustrating the tubular elbow in phantom;

FIG. 2 is a side elevational view of a portion of the tracheostomy tube assembly of the present invention;

FIG. 3 is a front elevational view of the flange member of the tracheostomy tube assembly of FIG. 1;

FIG. 4 is a top plan view of the tracheostomy tube assembly according to a second embodiment of the present invention;

FIG. 5 is a side elevational view of the tracheostomy tube assembly according to a second embodiment of the present invention;

FIG. 6 is a rear perspective view of the tracheostomy tube assembly according to both the first and second embodiments of the present invention; and FIG. 7 is a top sectional view of an inner cannula for use with tracheostomy tube assemblies constructed in accordance with either the first or second embodiments of the present invention.

DETAILED DESCRIPTION OF THE PREFERRED EMBODIMENT

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be also accomplished by different embodiments that are also intended to be encompassed within the spirit and scope of the invention.

Referring now to the drawings, FIG. 1 shows a front perspective view of a tracheostomy tube assembly 10 constructed in accordance with a first embodiment of the present invention. Tracheostomy tube assembly 10 generally comprises an arcuate cannula 12 having a first end 12a and a second end 12b, which is sized and configured to be insertable through a tracheostomy. When tracheostomy tube assembly 10 is in use, first end 12a as well as the major portion of the length of cannula 12 will reside within the trachea, with end 12b being generally flush with the anterior surface of the patient's neck. In the first embodiment, a tubular elbow 14 is mounted to the end of 12b cannula 12. Tubular elbow 14 defines a bend 16 which will be inferiorally directed and disposed immediately adjacent the neck when cannula 12 is inserted into the trachea. Bend 16 preferably has an angular disposition of about 40 degrees. Advantageously, tubular elbow 14 is pivotally connected to cannula 12 for reasons which will be explained in greater detail below. The end of tubular elbow 14 opposite that connected to cannula 12 has a ventilator tube connector 18 mounted thereon. In the preferred embodiment, the ventilator tube connector 18 comprises a male connector preferably formed of plastic, which is rotatably mounted to tubular elbow 14, though it will be appreciated that other connectors (e.g. ball and socket, female, etc.) may be utilized in place of the rotatable angled connector shown in FIG. 1. Thus, when an attendant ventilator tube is attached to ventilator tube connector 18, ventilator tube connector 18 and tubular elbow 14 will permit operative connection of the ventilator tube to cannula 12 in a manner such that the ventilator tube will extend inferiorally away from the chin when cannula 12 is inserted into the trachea. As previously specified, tubular elbow 14 is pivotally connected to the end 12b of cannula 12. The pivotal connection between elbow 14 and cannula 12 is facilitated by a pivotal connector 20. Pivotal connector 20, which is formed as part of and extends outwardly from a connector tab 19 allows tubular elbow 14 to be rotated about cannula 12. The rotational capacities of both tubular elbow 14 and ventilator tube connector 18 aid in avoiding problems associated with movement of the ventilator tube which would tend to twist the tube or dislodge the tracheostomy tube.

Referring now to FIGS. 1-3, in the preferred embodiment a flange member 22 extends laterally outward from the end 12b of cannula 12. Flange member 22 is configured in a manner so as to define an upper notch or recess 26 and a lower notch or recess 28 about end 12b of cannula 12 when attached thereto. Upper recess 26 and lower recess 28 serve to provide increased accessibility to the tracheostomy when cannula 12 is inserted into the trachea of a patient. In this regard, such increased accessibility allows for the cleaning, disinfection, etc. of the tracheostomy. In fabricating tracheostomy tube assembly 10, flange member 22 is formed about connector tab 19. As can be appreciated, the interface of connector tab 19 to flange member 22 facilitates the attachment of pivotal connector 20, which extends from tab 19, to flange member 22. In the preferred embodiment, connector tab 19 and flange member 22 are made from different materials. In this respect, connector tab 19 is preferably constructed from polycarbonate while flange member 22 is constructed from polyurethane. Advantageously, the utilization of these different materials aids in preventing the fracturing of flange member 22 or pivotal connector 20 when a lateral force is applied to tubular elbow 14 when connected to pivotal connector 20. Flange member 22 further defines outer surface 22a and inner surface 22b. When is inserted into the trachea, inner surface 22b of flange member 22 will come in direct contact with the anterior surface of the patient's neck. Disposed within outer surface 22a of flange member 22 is a first transversely extending slot 24 and a second transversely extending slot 25. Advantageously, slots 24, 25 are operable to allow flange member 22 to bend easily and thus match the contour of the patient's neck. Though slots 24, 25 are used in the preferred embodiment to facilitate the bending of flange member 22, it will be appreciated that any array of apertures or any other material disruption that will allow such bending to occur may be used as an alternative. As best seen in FIG. 2, the outer edges of inner surface 22a is radiused, contoured distally or feathered so as to eliminate sharp edges which could cut into the underlying skin of the neck. As also seen in FIG. 2, end 12b of cannula 12 includes an integral, reinforced angled outer surface 13. Typically, after cannula 12 has been inserted into the trachea, the stoma site will close after a period of time thereby seizing upon cannula 12 at a point adjacent end 12b thereof. In this respect, angled surface 13 is operable to facilitate the withdrawal of cannula 12 from the trachea after such seizing has occurred. Additionally, angled surface 13 further prevents cannula 12 from closing or collapsing when such closure of the stoma occurs.

Disposed within flange member 22 is a first neck strap aperture 30 and a second neck strap aperture 32. Apertures 30, 32 are adapted to permit attachment of a neck strap (not shown) to the tracheostomy tube assembly 10 in order to facilitate the attachment thereof to the neck of a patient. Disposed about the periphery of first neck strap aperture 30 is a first reinforcement rib 34 while disposed about the periphery of second neck strap aperture 32 is a second reinforcement rib 36, both of which are formed on outer surface 22a. Reinforcement ribs 34, 36 are used to provide additional structural support to flange member 22 so that the neck strap (not shown) is less likely to be torn from apertures 30, 32 during the tightening or adjustment of the neck strap. As an alternative to the use of a neck strap, flange member 22 includes suture holes 38, 40 respectively, which extend therethrough. In this regard, suture holes 38 which are disposed within first slot 24 and suture holes 40 which are disposed within second slot 25 may be used to suture flange member 22 directly to the anterior surface of the patient's neck.

Since the tracheostomy tube assembly 10 of the present invention is intended not to interfere with the chin of the patient, of great significance is the distance separating the neck of the patient from the inferiorally directed bend 16. In this regard, it is contemplated that the tracheostomy tube assembly 10 of the present invention will be fabricated in at least two different sizes. A first size will be used with neonates and infants, while a second size will be used with adult patients. Referring now to FIG. 1a, the distance "A" separating the center point P1 of inferiorally directed bend 16 and inner surface 22b of flange member 22 (i.e. the neck of the patient) when cannula 12 of the neonate/infant version of the present invention is inserted into the trachea is between 5 mm and 15 mm and preferably 10 mm. Similarly, the distance "B" separating the neck of the patient and the point P2 on tubular elbow 14 where bend 16 is completed, is between 12 mm and 24 mm and preferably 18 mm. In the adult version, the distance "A" separating center point P1 of bend 16 and the neck of the patient is between 15 mm and 25 mm and preferably 20 mm. Similarly, the distance "B" separating the neck of the patient and point P2 of the tubular elbow 14 of the adult version is between 22 mm and 34 mm and preferably 28 mm.

Referring now to FIG. 1, the tracheostomy tube assembly 10 of the present invention further comprises a tubular extension member 42 having a female adaptor 44 formed on one end thereof. In the preferred embodiment, female adaptor 44 is sized and configured to slidably receive ventilator tube connector 18. Formed on the end of tubular extension member 42 opposite that which includes female adaptor 44, is a male connector 45. Male connector 45 preferably has the same size and configuration as ventilator tube connector 18 formed on tracheostomy tube assembly 10 itself. Advantageously, extension member 42 is angled such that, when connected to ventilator tube connector 18, extension member 42 will extend downwardly over the anterior thorax to permit attachment thereto of an attendant ventilator tube. Formed within the female adaptor 44 of tubular extension member 42 is a suction catheter introduction port 46. In this respect, suction catheter port 46 is operable to permit passage of a suction catheter therethrough into cannula 12. A plug 48 which is attached to extension member 42 is used to block suction catheter port 46 when such is not being used. Such plug 48 may be formed of any suitable material and is preferably formed from a plastic which is somewhat softer and/or more compressible than the material of which the surrounding female adaptor 44 is formed so as to facilitate frictional engagement and holding of plug 48 within port 46.

Referring now to FIGS. 4 and 5, illustrated is a second embodiment of the present invention wherein tubular elbow 14 is replaced by a ball and socket connector 50. As with tubular elbow 14, ball and socket connector 50 is operable to define an inferiorally directed bend immediately adjacent the anterior surface of the patient's neck when cannula 12 is inserted into the trachea. Ball and socket connector 50 is also adapted to permit operative connection of a ventilator tube to cannula 12 such that the ventilator tube will extend inferiorally away from the chin. As best seen in FIG. 5, one end of ball and socket connector 50 is attached to end 12b of cannula 12 while the other end includes a male connector 52 formed thereon which is sized and configured to be received into female adaptor 44 of tubular extension 42. As will be appreciated, ball and socket connector 50 will be sized such that the distance separating point P3 of male connector 52 will correspond to distance "B" as previously described with respect to the neonate/infant and adult versions of the first embodiment. Additionally, ball-and socket connector 50 may be formed as part of and extend outwardly from a connector tab as described above, thereby allowing flange member 22 of the second embodiment and ball and socket connector 50 to be constructed from different materials. As in the first embodiment, tubular extension 42 will extend downwardly over the anterior thorax to permit attachment thereto of an attendant ventilator tube.

Referring now to FIG. 6, illustrated is a rear perspective view of both the first and second embodiments of the present invention. An optional inflatable cuff 54 is disposed about a portion of cannula 12 between the first and second ends 12a, 12b thereof. A tube 56 extends from inflatable cuff 54, along cannula 12 and into a bladder 58. The squeezing of bladder 58 is operable to inflate cuff 54. A valve 60 disposed on the bottom of bladder 58 is operable to deflate cuff 54. Cuff 54 is used to provide a seal between the external surfaces of cannula 12 and the internal surfaces of the trachea into which cannula 12 is inserted and may be used on both the neonate/infant and adult versions of the present invention.

Referring now to FIG. 7, illustrated is an inner cannula assembly 62 which is adapted to be used with a tracheostomy tube assembly 10 constructed in accordance with either the first or second embodiments of the present invention. Since phlegm and mucus often form within the tracheal tubing, one of the primary purposes of inner cannula 62 is to allow the cleaning of tracheostomy tube assembly 10 without the removal thereof from the patient. Inner cannula assembly 62 generally comprises an elongate inner cannula portion 64 which is sized and configured to be receivable within cannula 12 of tracheostomy tube assembly 10. Disposed on one end of inner cannula 64 is a connector portion 66. Advantageously, connector portion 66 is sized and configured to be receivable within the recess 68 defined by ventilator tube connector 18. Connector portion 66 further comprises an outwardly extending flange 70 formed on the outermost end thereof. Flange 70 is adapted to rest upon the outer rim of ventilator tube connector 18 and may be grasped by the hand of a user to pull inner cannula assembly 62 from tracheostomy tube assembly 10. Also disposed about the outer surface of connector portion 66 is a sealing member 72. Sealing member 72 is sized and configured to be received within a notch 74 defined within recess 68 of ventilator tube connector 18 in snap-like fashion, thereby providing an air-tight seal between connector portion 66 and tracheostomy tube assembly 10. It will be appreciated that inner cannula assembly 62 is not necessary for the proper utilization of tracheostomy assembly 10 but serves only as an added component which may utilized therewith.

What is claimed is:

1. A tracheostomy tube comprising:
a generally arcuate cannula having a first end, a second end, and a hollow lumen extending therethrough, said cannula lumen being of substantially constant transverse dimension from the first end thereof to the second end thereof, said cannula being sized and configured to be insertable through a tracheostomy to a first portion whereat the first end of the cannula resides within the trachea of the patient and the second end of the cannula is substantially flush with the anterior surface of the neck of a patient;

a flange member having an inner surface and an outer surface, said flange member extending laterally outward from the cannula such that the inner surface of the flange member will abut against the anterior surface of the neck of the patient when the cannula is inserted in said first position; and a ball and socket connector having a proximal end, a distal end and a hollow bore extending therethrough, the proximal end of said ball and socket connector being connected to the second end of said cannula such that the bore of said ball and socket connector is in fluid connection and direct alignment with the lumen of said cannula.

2. The tracheostomy tube of claim 1 wherein said ball and socket connector is adapted to form a bend of 30 to 60 degrees.

3. The tracheostomy tube of claim 2 wherein said ball and socket connector forms a bend of approximately 40 degrees.

4. The tracheostomy tube of claim 1 further comprising:
a ventilator tubing connector connected to the distal end of the ball and socket connector.

5. The tracheostomy tube of claim 4 wherein the ventilator tubing connector comprises a cylindrical member formed on the distal end of the ball and socket connector.

6. The tracheostomy tube of claim 3 wherein the distance separating the distal end of the ball and socket connector and the inner surface of the flange member which abuts the anterior surface of the neck of the patient is between 12 mm and 24 mm.

7. The tracheostomy tube of claim 6 wherein the distance separating the distal end of the ball and socket connector and the inner surface of the flange member which abuts the anterior surface of the neck of the patient is approximately 18 mm.

8. The tracheostomy tube of claim 3 wherein the distance separating the distal end of the ball and socket connector and the inner surface of the flange member which abuts the anterior surface of the neck of the patient is between 22 mm and 34 mm.

9. The tracheostomy tube of claim 8 wherein the distance separating the distal end of the ball and socket connector and the inner surface of the flange member which abuts the anterior surface of the neck of the patient is approximately 28 mm.

10. The tracheostomy tube of claim 1 wherein said cannula is further configured such that a portion of said cannula adjacent the inner surface of said flange member is of gradually enlarging diameter so as to facilitate ease of cannula extraction from the tracheostomy.

11. The tracheostomy tue of claim 1 wherein said flange is formed to have at least one stomal site access notch formed in said flange so as to expose a portion of the tracheostomy into which the cannula is inserted.

12. The tracheostomy tube of claim 11 wherein said at least one stomal site access notch comprises:
a first stomal site access notch formed in said flange at a location above said cannula; and
a second stomal site access notch formed in said flange at a location below said cannula.

13. The tracheostomy tube of claim 11 wherein the inner surface of said flange member is formed of rounded contour to prevent irritation of the neck of the patient.

14. The tracheostomy tube of claim 13 further comprising a plurality of strap connecting apertures formed in the flange member to permit attachment of a neck strap thereto.

15. The tracheostomy tube of claim 14 wherein said flange member further comprises reinforced areas formed next to said strap connecting apertures to deter tearing of said flange member by a neck strap connected thereto.

16. The tracheostomy tube of claim 13 further comprising a plurality of suture connecting apertures formed in the flange member to facilitate suturing of the flange member to the neck of the patient.

17. The tracheostomy tube of claim 1 wherein said flange member further comprises:
a flexible outer flange body;
a tab member disposed at least partially within said outer flange body adjacent the second end of said cannula, said tab member being more rigid than said outer flange body; and
an annular connector ring formed on and extending from said tab member such that said connector ring is substantially continuous with the second end of said cannula, said connector ring being configured to receive and attach to the proximal end of said ball and socket connector.

18. The tracheostomy tube of claim 17 wherein the tab member and rotatable connector are formed of polycarbonate and the outer flange body is formed of polyurethane.

19. The tracheostomy tube of claim 1 further comprising an inflatable cuff disposed about the cannula between the first and second end thereof.

20. A tracheostomy tube assembly comprising the tracheostomy tube of claim 4 in combination with a tubular extension having a first end connectable to said ventilator tubing connector and a second end connectable to a separate ventilator tube.

21. The tracheostomy tube assembly of claim 20 further comprising an angled connector formed on the first end of said tubular extension.

22. The tracheostomy tube assembly of claim 20 wherein a suction catheter introduction port is formed in the tubular extension to permit insertion of a suction catheter thereinto.

23. The tracheostomy tube of claim 4 further comprising an inner cannula which is slidably insertable and removable from the ventilator tubing connector and the cannula.

24. A tracheostomy tube insertable into a tracheostomy formed in the neck of a human patient, said tracheostomy tube comprising:
a generally arcuate cannula having a proximal end, a distal end and a hollow lumen extending therethrough, said cannula lumen being of substantially constant transverse dimension from the proximal end thereof to the distal end thereof, said canula being sized and configured to be inserted, distal end first, through said tracheostomy;
a flange member having an inner surface and an outer surface, said flange member extending laterally from said cannula such that, when said cannula is inserted into said tracheostomy, said tracheostomy tube may be advanced to an operative position whereat said inner surface of said flange abuts against the anterior surface of the neck of said patient; and a tubular elbow rotatably connected to said proximal end of said cannula adjacent said outer surface of said flange, said tubular elbow having a hollow bore extending therethrough, said hollow bore of said elbow being in fluid connection and direct alignment with the lumen of said cannula.

25. The tracheostomy tube of claim 24 wherein said tubular elbow comprises a tubular elbow having a bend of thirty to sixty degrees.

26. The tracheostomy tube of claim 25 wherein said tubular elbow forms a bend of approximately forty degrees.

27. The tracheostomy tube of claim 24 further in combination with a ventilator tubing connector component comprising a cylindrical tubular member rotatably engageable with and mountable on said rotatable tubular elbow so as to be rotatable relative to said tubular elbow.

28. The tracheostomy tube of claim 24 wherein the distance from the inner surface of said flange to the opposite end of said tubular elbow is between 22 mm and 34 mm.

29. The tracheostomy tube of claim 28 wherein said distance is approximately 28 mm.

30. A tracheostomy tube insertable into a tracheostomy formed in the neck of a patient, said tracheostomy tube comprising:

a generally arcuate cannula having a proximal end, a distal end and a hollow lumen extending longitudinally therethrough, said cannula being sized and configured to be insertable, distal end first, through said tracheostomy;

a flange member having an inner surface and an outer surface, said flange member extending laterally from the proximal end of said cannula such that said cannula may be inserted, distal end first, into said tracheostomy and advanced to an operative position whereat the inner surface of said flange member abuts against the neck of said patient;

an angular tube member mounted outboard of the outer surface of said flange, said angular tube member forming a bend of 30 to 60 degrees, and having a first end, a second end and a hollow bore extending therethrough, the first end of said angular tube member being mounted to the outer surface of said flange and the hollow bore of said angular tube member being fluidly connected and aligned with the lumen of said cannula to permit respiratory airflow through said cannula lumen and through the hollow bore of said angular tube member.

31. The tracheostomy tube of claim 30 wherein said angular tube member comprises a tubular elbow having a first end and a second end, the first end of said tubular elbow being rotatably mounted to the outer surface of said flange such that said tubular elbow is rotatable relative to the flange.

32. The tracheostomy tube of claim 30 wherein said angular tube member comprises a ball and socket connector having a first end and a second end, the first end of said ball and socket connector being rigidly mounted to the outer surface of said flange and the ball and socket thereof being bendable to form said bend of 30 to 60 degrees and being rotatable to permit relative rotation of the second end of said ball and socket connector relative to said flange.

33. The tracheostomy tube of claim 30 wherein the distance from the inner surface of said flange to the second end of said angular tubular member is 22 mm to 34 mm.

* * * * *